(12) United States Patent
Bilodeau et al.

(10) Patent No.: US 8,252,799 B2
(45) Date of Patent: Aug. 28, 2012

(54) HEXAHYDRO-1H-4,7-METHANOISOINDOLE-1,3-DIONE COMPOUNDS

(75) Inventors: Mark T. Bilodeau, Lansdale, PA (US); Kausik K. Nanda, Norristown, PA (US); B. Wesley Trotter, Glenside, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 144 days.

(21) Appl. No.: 12/530,944

(22) PCT Filed: Apr. 3, 2008

(86) PCT No.: PCT/US2008/004336
§ 371 (c)(1),
(2), (4) Date: Sep. 11, 2009

(87) PCT Pub. No.: WO2008/124030
PCT Pub. Date: Oct. 16, 2008

(65) Prior Publication Data
US 2010/0105697 A1    Apr. 29, 2010

Related U.S. Application Data

(60) Provisional application No. 60/921,759, filed on Apr. 4, 2007.

(51) Int. Cl.
A61K 31/496    (2006.01)
C07D 417/12    (2006.01)
(52) U.S. Cl. .................... 514/254.04; 544/368
(58) Field of Classification Search .................. None
See application file for complete search history.

(56) References Cited

U.S. PATENT DOCUMENTS

| | | | | |
|---|---|---|---|---|
| 4,366,172 A | * | 12/1982 | Lednicer | 514/646 |
| 4,745,117 A | | 5/1988 | Ishizumi et al. | |
| 5,219,879 A | * | 6/1993 | Ko et al. | 514/438 |
| 5,532,372 A | | 7/1996 | Saji et al. | |
| 5,780,632 A | | 7/1998 | Saji et al. | |
| 7,605,260 B2 | | 10/2009 | Kakiya et al. | |
| 2006/0142276 A1 | | 6/2006 | Ohno et al. | |
| 2008/0255148 A1 | | 10/2008 | Ohno et al. | |
| 2009/0076027 A1 | | 3/2009 | Czarnik | |

FOREIGN PATENT DOCUMENTS

| | | |
|---|---|---|
| EP | 0 464 846 | 7/1991 |
| JP | 8-333368 | * 12/1996 |
| JP | 8333368 A | 12/1996 |
| WO | WO2011002103 | 1/2011 |

OTHER PUBLICATIONS

Mayumi et al. Chemical Abstracts, vol. 126 No. 30466h, Abstract for JP 8-333368 (Dec. 17, 1996) (1997).*
Abstract for JP8333368 (Dec. 17, 1996), Obtained online from http://v3.espacenet.com/publicationDetails/biblio?DB=EPOOC&adjacent=true&locale=en_ep&FT=D&date= ... Mar. 26, 2011.*
Dodd et al. Current Drug Safety vol. 1, pp. 25-33 (2006).*
Perrone et al. J. Med. Chem. vol. 37,pp. 99-104.*
Jones et al. Pharmacology, Biochemistry and Behavior, vol. 71, p. 555-568 (2002).*
Robichaud et al. in Annual Reports in Medicinal Chemistry, vol. 36, p. 11-20 (2000).*
Kossakowski et al. Chemical Abstracts, vol. 128, No. 244028 (1998) Abstract for Acta Poloniae Pharmaceutica 54(6), pp. 479-481 (1997).*
K. Ishizumi et al., "Succinimide Derivatives. II. Synthesis and Antipsychotic Activity of N-[4-[4-(1,2-Benzisothiazol-3-yl)-1-Piperazinyl]butyl]-1,2-Cis-Cyclohexandedicarboximide (SM-9018) and Related Compounds", Chem. Pharm. Bull., vol. 43, vol. 12, pp. 2139-2151, XP001026361, 1995.
J. A. Cipollina et al., "Synthesis and Biological Activity of the Putative Metabolites of the Atypical Antipsychotic Agent Tiospirone", J. Med. Chem, vol. 34, pp. 3316-3328, XP002157852, 1991.
P. Cole et al, "Lurasidone Hydrochloride", Drugs of the Future, vol. 33, pp. 316-322, 2008.
T. Horisawa et al., "The Effects of Selective Antagonists of Serotonin 5-HT7 and 5-HT1a Receptors on Mk-801-Induced impairment of learning and memory in the passive avoidance and Morris Water Maze Tests in Rats: Mechanistic Implications for the Beneficial Effects of the Novel Atypical Antipsychotic Lurasidone", Behavioral Brain Research, vol. 220, pp. 83-90, 2011.
T. Ishibashi et al., "Pharmacological Profile of Lurasidone, a Novel Antipsychotic Agent with Potent 5-Hydroxytryptamine 7 (5-HT7) and 5-HT1A Receptor Activity" Pharmacology and Experimental Therapeutics, vol. 334, pp. 171-181, 2010.
T. Ishiyama et al., "Lurasidone (SM-13496), A Novel Atypical Antipsychotic Drug, Reverses MK-801-Induced Impariment of Learning and Memory in the Rat Passive-Avoidance Test", E. Journal of Pharmacology, vol. 572, pp. 160-170, 2007.

(Continued)

*Primary Examiner* — Emily Bernhardt
(74) *Attorney, Agent, or Firm* — J. Eric Thies; Gerard M. Devlin

(57) ABSTRACT

The present invention is directed to therapeutic agents of the formula (I) which are atypical antipsychotics and which are useful in the treatment of neurological and psychiatric disorders associated with dopamine D2 and serotonin 5-HT2A neurotransmission dysfunction. wherein; $R^1$ is $C_1$-6alkyl, which is unsubstituted or substituted with 1-6 fluoro, wherein $R^1$ and the hydroxyl group on the ring are attached to the same carbon atom; or a pharmaceutically acceptable salt thereof.

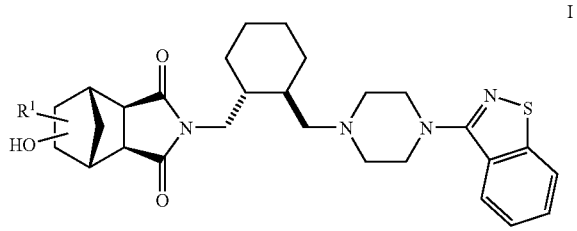

8 Claims, No Drawings

OTHER PUBLICATIONS

Meyer et al., "Lurasidone: a new drug in development for schizophrenia", Expert Opin Investig Drugs, 18(11), pp. 1715-1726, 2009.

M. Nakamura et al., "Lurasidone in the Treatment of Acute Schizophrenia: A Double-Blind, Placebo-Controlled Trial", J. Clin. Psychiatry, pp. e1-e8, 2009.

Communication from European Patent Office for EPO Patent Application No. 08 742 520.3 (Jul. 22, 2010).

Response submitted in EPO Patent Application No. 08 742 520.3 (Sep. 23, 2010).

Written Opinion from Singapore Patent Office for Singapore Patent Application No. 200906459-3 (Nov. 19, 2010).

S. Caccia et al., "Pharmacokinetics and Metabolism Update for Some Recent Antipsychotics", Expert Opinion Drug Metab. Toxicol., 2011, pp. 829-846.

L. Citrome et al., "Lurasidone for Schizophrenia: A Review of the Efficacy and Safety Profile for this Newly Approved Second-Generation Antipsychotic", Int. J. Clin. Pract, 2011, pp. 189-210, vol. 65.

M. Cruz et al., "Lurasidone HCl (Latuda), an Oral, Once-Daily Atypical Antipsychotic Agent for the Treatment of Patients with Schizophrenia", Drug Forecast, 2011, pp. 489-492, vol. 36.

T. Ishibashi et al., "Pharmacological profile of Lurasidone, a Novel Antipsychotic Agent with Potent 5-Hydroxytryptamine 7 (5-HT7) and 5-HT1A Receptor Activity", J. Pharmacology and Experimental Therapeutics, 2010, vol. 171-181, vol. 334.

J. Meyer et al., "Luasidone: A New Drug in Development for Schizophrenia", Drug Evaluation, 2009, pp. 1715-1726, vol. 18.

PCT International Preliminary Examination Report for PCT/US2008/004336 (Oct. 15, 2009).

* cited by examiner

HEXAHYDRO-1H-4,7-METHANOISOINDOLE-1,3-DIONE COMPOUNDS

CROSS REFERENCE TO RELATED APPLICATIONS

This application is a U.S. National Phase application under 35 U.S.C. §371 of PCT Application No. PCT/US2008/004336, filed Apr. 3, 2008, which claims priority under 35 U.S.C. §119(e) from U.S. Ser. No. 60/921,759, filed Apr. 4, 2007.

BACKGROUND OF THE INVENTION

Schizophrenia is a debilitating psychiatric disorder characterized by a combination of negative (blunted affect, withdrawal, anhedonia) and positive (paranoia, hallucinations, delusions) symptoms as well as marked cognitive deficits. While the etiology of schizophrenia is currently unknown, the disease appears to be produced by a complex interaction of biological, environmental, and genetic factors. Atypical antipsychotics form the front line in the treatment of schizophrenia and more recently in bipolar disorder. However, up to 30% of schizophrenic patients are not adequately treated by currently available medication. While there are a number of atypical antipsychotic agents currently available, these agents suffer from a high rate of discontinuation due to either patient and/or physician dissatisfaction with efficacy or safety/tolerability. Atypical antipsychotics possess a pharmacology which is thought to underlie their ability to achieve efficacy at positive symptoms via antagonism at dopamine D2 and serotonin 5-$HT_{2A}$ receptors. These activities produce some efficacy on negative symptoms but also contribute to adverse side effects. These adverse side effects include weight gain/metabolic effects (thought to be associated with antagonism at 5-$HT_{2C}$ and antagonism at histamine H1 receptors), extrapyramidal effects and prolactin secretion (thought to be associated with antagonism at dopamine D2 receptors), sedation (thought to be associated with antagonism at α1 adrenergic and antagonism at histamine H1 receptors) and cognitive impairment (thought to be associated with antagonism at muscarinic M1 receptors). Accordingly, there is a need in the art for atypical antipsychotic agents with better efficacy on positive symptoms, negative symptoms and/or decreased adverse side effects.

SUMMARY OF THE INVENTION

The present invention is directed to therapeutic agents which are atypical antipsychotics and which are useful in the treatment of neurological and psychiatric disorders associated with dopamine D2 and serotonin 5-HT2A neurotransmission dysfunction.

DETAILED DESCRIPTION OF THE INVENTION

The present invention is directed to compounds of the formula I:

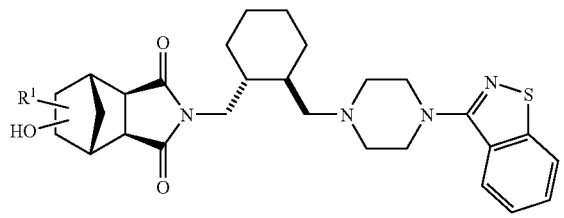

wherein:

$R^1$ is $C_{1-6}$alkyl, which is unsubstituted or substituted with 1-6 fluoro, wherein $R^1$ and the hydroxyl group on the ring are attached to the same carbon atom;

or a pharmaceutically acceptable salt thereof.

Within this embodiment, the present invention includes compounds wherein $R^1$ is $C_{1-3}$alkyl which is unsubstituted or substituted with 1-6 fluoro.

Further within this embodiment, the present invention includes compounds wherein $R^1$ is selected from the group consisting of:

(1) methyl,
(2) ethyl,
(3) n-propyl,
(4) isopropyl,
(5) trifluoromethyl, and
(6) trifluoroethyl.

Further within this embodiment, the present invention includes compounds wherein $R^1$ is methyl. Also further within this embodiment, the present invention includes compounds wherein $R^1$ is ethyl. Also further within this embodiment, the present invention includes compounds wherein $R^1$ is trifluoromethyl.

An embodiment of the present invention includes compounds of the formula Ia:

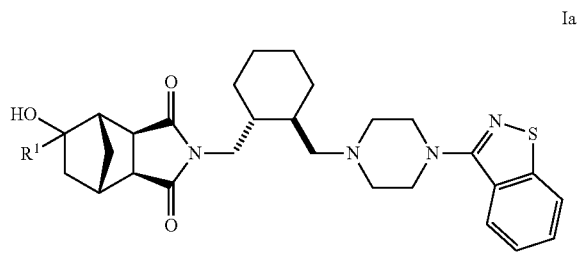

wherein $R^1$ is defined herein;

or a pharmaceutically acceptable salt thereof.

An embodiment of the present invention includes compounds of the formula Ia':

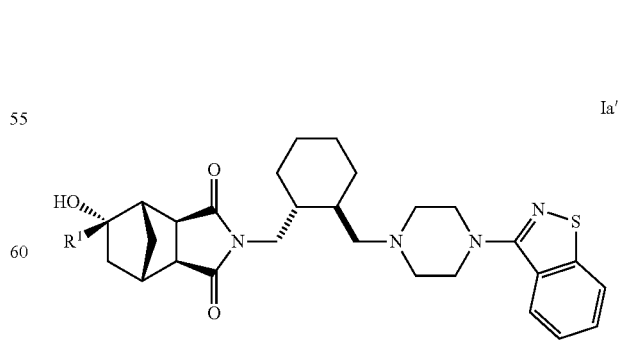

wherein $R^1$ is defined herein;

or a pharmaceutically acceptable salt thereof.

An embodiment of the present invention includes compounds of the formula Ib:

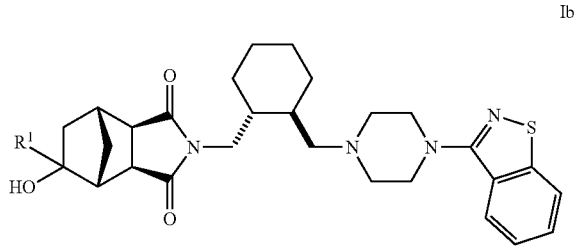

wherein $R^1$ is defined herein;
or a pharmaceutically acceptable salt thereof.

An embodiment of the present invention includes compounds of the formula Ib':

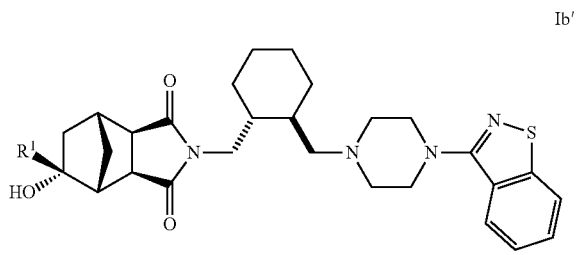

wherein $R^1$ is defined herein;
or a pharmaceutically acceptable salt thereof.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more chiral centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts. Exemplifying the invention is the use of the compounds disclosed in the Examples and herein.

The subject compounds are useful in a method of treating a neurological or psychiatric disorder associated with dopamine D2 and serotonin 5-HT2A neurotransmission dysfunction in a patient such as a mammal in need of such inhibition comprising the administration of an effective amount of the compound. In addition to primates, especially humans, a variety of other mammals can be treated according to the method of the present invention.

The present invention is further directed to a method for the manufacture of a medicament for treating neurological or psychiatric disorder associated with dopamine D2 and serotonin 5-HT2A neurotransmission dysfunction in humans and animals comprising combining a compound of the present invention with a pharmaceutical carrier or diluent.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof. The terms "administration of" and or "administering a" compound should be understood to mean providing a compound of the invention or a prodrug of a compound of the invention to the individual in need of treatment.

The utility of the compounds in accordance with the present invention as atypical antipsychotics may be demonstrated by methodology well known in the art. In particular, the compounds of the following examples had activity in reference assays by exhibiting high affinity antagonism for dopamine D2, serotonin 5-HT2A, α2C adrenergic receptors, partial agonism at 5-HT1A receptors and weak affinity at 5-HT2C, histamine H1 and M1 receptors.

With respect to other imide compounds such as those disclosed in U.S. Pat. No. 5,532,372 (issued Jul. 2, 1996) and Japanese Patent Application JP 8-333368 (published Dec. 17, 1996), the present compounds exhibit unexpected properties, such as with respect to increased metabolic stability, oral bioavailability, safety and/or selectivity with respect to relevant receptors. In general, the present compounds possess relatively high affinity antagonism for dopamine D2, serotonin 5-HT2A, α2C adrenergic receptors, partial agonism at 5-HT1A receptors and weak affinity at 5-HT2C, histamine H1 and M1 receptors. Based on this receptor profile, the present compounds are expected to have efficacy on positive and negative symptoms of schizophrenia. The present compounds are also expected to be relatively well tolerated. The present compounds are also expected to have a lower propensity for weight gain and treatment related metabolic disorders relative to currently-marketed atypical antipsychotics.

The compounds of the present invention have utility in treating a variety of neurological and psychiatric disorders, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

Of the disorders above, the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In a specific embodiment, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In another specific embodiment, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In another specific embodiment, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the Diagnostic and Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In another specific embodiment, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In another specific embodiment, the present invention provides a method for treating obesity or eating disorders associated with excessive food intake and complications associated therewith, comprising: administering to a patient in need thereof an effective amount of a compound of the present invention. At present, obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-IV-TR. The skilled artisan will recognize that there are alternative nomenclatures, nosologies and classification systems for general medical conditions, and that these systems evolve with medical and scientific progress. Thus the term "obesity or eating disorders associated with excessive food intake" is intended to include like conditions and disorders that are described in other diagnostic sources.

The subject compounds are further useful in a method for the prevention, treatment, control, amelioration, or reeducation of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5\text{-HT}_{1A}$ agonists or antagonists, especially $5\text{-HT}_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art.

The subject compounds are further useful in a method for the prevention, treatment, control, amelioration, or reeducation of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLE 1

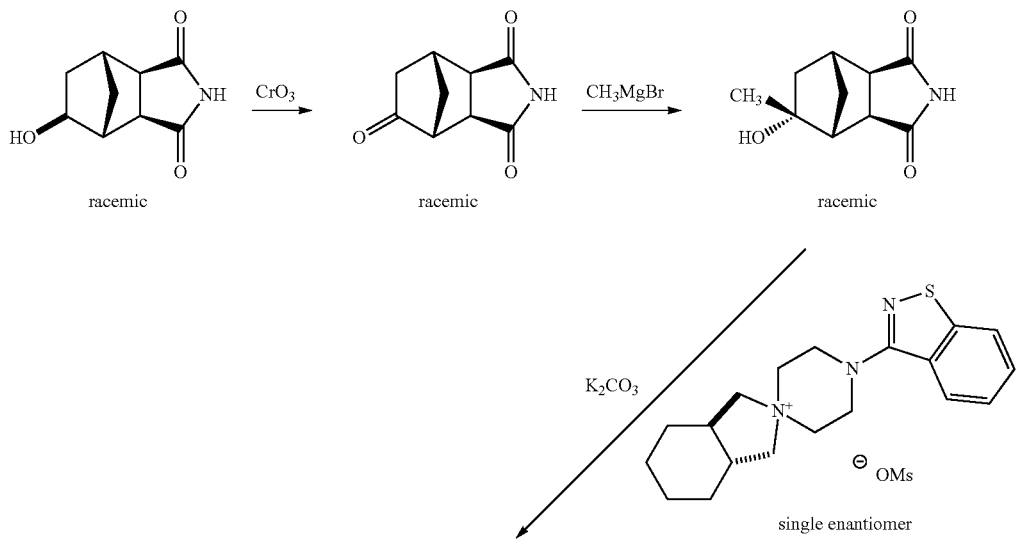

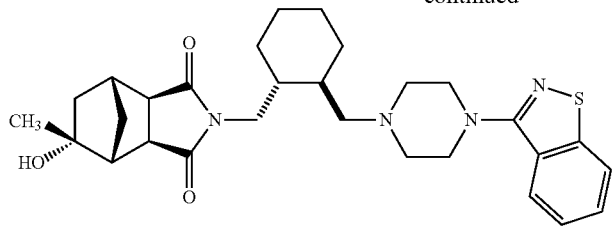

and

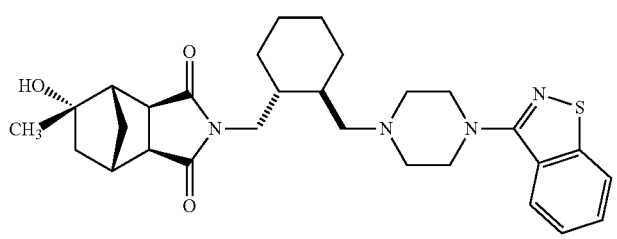

(Separated by chiral HPLC)

Step 1: rac-(3aS,4S,7S,7aR)-tetrahydro-1H-4,7-methanoisoindole-1,3,5(4H)-trione

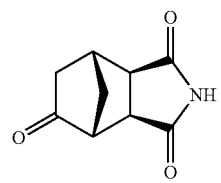

Chromium trioxide (2.7 g) was dissolved in concentrated sulfuric acid (2.3 mL) and water (10 mL). 12.17 mL of this solution was added dropwise to a 0° C. solution of rac-(3aS,4R,5S,7R,7aR)-5-hydroxyhexahydro-1H-4,7-methanoisoindole-1,3-dione (4.21 g) (prepared by modification of the procedures in Japanese Patent Publication JP 8-333368, Dec. 17, 1996) in 20 mL of acetone. After 1 hr, 2-propanol (20 mL) was added, and the reaction was stirred 30 min (orange color dissipates). The reaction was filtered through celite and concentrated in vacuo. Silica gel chromatography eluting with 98:2 $CH_2Cl_2$:MeOH afforded 4 g of the titled compound as a white solid.

Step 2: rac-(3aS,4S,5R,7S,7aR)-5-hydroxy-5-methylhexahydro-1H-4,7-methanoisoindole-1,3-dione

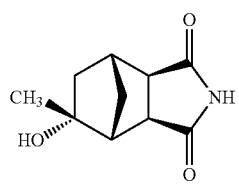

To a −78° C. solution of rac-(3aS,4S,7S,7aR)-tetrahydro-1H-4,7-methanoisoindole-1,3,5(4H)-trione (1.08 g, 6.03 mmol) (Kossakowski, Jerzy; Zawadowski, Teodor; Balicka, Eliza., *Acta Poloniae Pharmaceutica* (1997), 54(6), 479-481) in 50 ml of anhydrous THF was added methylmagnesium bromide (5.02 ml of a 3 M solution in THF, 15.07 mmol). After 2 hr, an additional 3 mL of methylmagnesium bromide solution was added. After another 2 hr, an additional 2 mL of methylmagnesium bromide solution was added. After 6 hr total at −78° C., the cooling bath was removed and the reaction allowed to warm to room temperature. The reaction was quenched with acetic acid (1.725 ml, 30.1 mmol) (Carefully). 200 uL of water was added, and the mixture was diluted with $CH_2Cl_2$ and 2 mL MeOH. The mixture was dried over $Na_2SO_4$, filtered, and concentrated to give a white foam. The foam was dissolved in 5% MeOH/$CH_2Cl_2$ and filtered through a plug of silica to give the titled compound as an off-white solid.

Step 3: (3aS,4S,5R,7S,7aR)-2-[((1R,2R)-2-{[4-(1,2-benzisothiazol-3-yl)piperazin-1-yl]methyl}cyclohexyl)methyl]-5-hydroxy-5-methylhexahydro-1H-4,7-methanoisoindole-1,3-dione

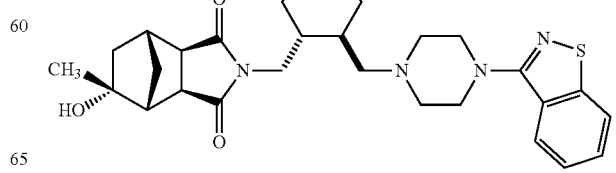

and (3aR,4S,5S,7S,7aS)-2-[((1R,2R)-2-{[4-(1,2-benzisothiazol-3-yl)piperazin-1-yl]methyl}cyclohexyl)methyl]-5-hydroxy-5-methyl-hexahydro-1H-4,7-methanoisoindole-1,3-dione

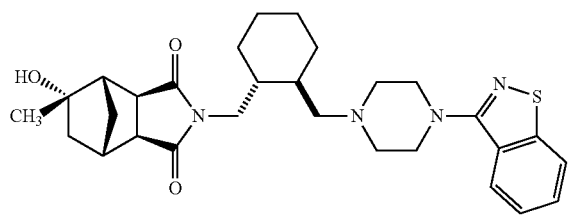

To a solution of rac-(3aS,4S,5R,7S,7aR)-5-hydroxy-5-methylhexahydro-1H-4,7-methanoisoindole-1,3-dione (88 mg, 0.451 mmol) in toluene (5 ml) and DMF (1.8 ml) were added trans-R,R-3a,7a-octahydroisoindolium-2-spiro-1'-[4'-(1,2-benzoisothiazol-3-yl)]piperazine methanesulfonate (191 mg, 0.451 mmol) and potassium carbonate (125 mg, 0.902 mmol). The reaction was heated at 110° C. for 23 h, then removed from heat. The mixture was partitioned between ethyl acetate and water, and the aqueous solution was washed once more with ethyl acetate. The combined organic solutions were dried (Na$_2$SO$_4$) and concentrated. The residue was purified by silica gel chromatography eluting with EtOAc/hexanes to give 189 mg of a mixture of the two titled compounds. Preparative HPLC (Chiralcel OD, 60% EtOH/hexanes+0.1% diethylamine) provided: (3aS,4S,5R,7S,7aR)-2-[(1R,2R)-2-{[4-(1,2-benzisothiazol-3-yl)piperazin-1-yl]methyl}cyclohexyl)methyl]-5-hydroxy-5-methylhexahydro-1H-4,7-methanoisoindole-1,3-dione and (3aR,4S,5S,7S,7aS)-2-[((1R,2R)-2-{[4-(1,2-benzisothiazol-3-yl)piperazin-1-yl]methyl}cyclohexyl)methyl]-5-hydroxy-5-methylhexahydro-1H-4,7-methanoisoindole-1,3-dione. (3aS,4S,5R,7S,7aR)-2-[((1R,2R)-2-{[4-(1,2-benzisothiazol-3-yl)piperazin-1-yl]methyl}cyclohexyl)methyl]-5-hydroxy-5-methylhexahydro-1H-4,7-methanoisoindole-1,3-dione.
Retention time 4.6 min. $^1$H NMR (CDCl$_3$) δ 7.91 (d, 1H, J=8 Hz); 7.80 (d, 1H, J=8 Hz); 7.46 (t, 1H, J=8 Hz); 7.35 (t, 1H, J=8 Hz); 3.94 (dd, 1H, J=13, 4 Hz); 3.53 (t, 3H, J=5 Hz); 3.50 (d, 1H, J=7 Hz); 3.34 (dd, 1H, J=13, 10 Hz); 2.73 (d, 1H, J=7 Hz); 2.68-2.59 (m, 6 H); 2.48 (s, 1H); 2.23 (dd, 1H, J=13, 7 Hz); 1.89 (br d, 1H, J=14 Hz); 1.74 (dd, 1H, J=13, 5 Hz); 1.67 (br d, 2H, J=12 Hz); 1.61-1.51 (m, 3H); 1.48 (d, 2H, J=11 Hz); 1.41 (s, 3H); 1.38 (dd, 1H, J=13, 3 Hz); 1.27-1.09 (m, 4H); 1.06-0.96 (m, 2H). HRMS (ESI) calcd for C$_{29}$H$_{38}$N$_4$O$_3$S: 523.2738 [M+H]$^+$; found: 523.2713. In Vitro Affinity (Ki) on Human Receptors: 5HT1A (native) 8 nM; α2C 9 nM; α2A 59 nM; D2 1 nM; 5HT2A <10 nM; D3 2 nM; 5HT2C 16 nM; H1 371 nM; D1 457 nM; α1A 31 nM; α1D 82 nM; hERG 644 nM. Functional Potency (IC50) on Human Receptors: 5HT1A EC50=98 (77% max); α2C 160 nM; α2A 1217 nM; 5HT2A 32 nM; D2 25 nM; D1 1650 nM; 5HT2C 1707 nM; H1 3100 nM; hERG 4000 nM. (3aR,4S,5S,7S,7aS)-2-[((1R,2R)-2-{[4-(1,2-benzisothiazol-3-yl)piperazin-1-yl]methyl}cyclohexyl)methyl]-5-hydroxy-5-methylhexahydro-1H-4,7-methanoisoindole-1,3-dione. Retention time 5.2 min. $^1$H NMR (CDCl$_3$) δ 7.91 (d, 1H, J=8 Hz); 7.80 (d, 1H, J=8 Hz); 7.46 (t, 1H, J=8 Hz); 7.35 (t, 1H, J=8 Hz); 3.95 (dd, 1H, J=13, 4 Hz); 3.53 (t, 3H, J=5 Hz); 3.50 (d, 1H, J=7 Hz); 3.34 (dd, 1H, J=13, 10 Hz); 2.73 (d, 1H, J=7 Hz); 2.68-2.59 (m, 6H); 2.48 (s, 1H); 2.23 (dd, 1H, J=13, 7 Hz); 1.89 (br d, 1H, J=13, 5 Hz); 1.70-1.46 (m, 7H); 1.41 (s, 3H); 1.37 (dd, 1H, J=13, 3 Hz); 1.27-1.09 (m, 4H); 1.06-0.96 (m, 2H). HRMS (ESI) calcd for C$_{29}$H$_{38}$N$_4$O$_3$S: 523.2738 [M+H]$^+$; found: 523.2709.

Compounds in Table 1 were synthesized as shown above, but substituting the appropriately substituted rac-(3aS,4S,5R,7S,7aR)-5-hydroxy-5-alkylhexahydro-1H-4,7-methanoisoindole-1,3-dione as described in the Schemes and the foregoing examples. The requisite starting materials were commercially available, described in the literature or readily synthesized by one skilled in the art of organic synthesis.

TABLE 1

| Compound | Nomenclature | MS M + 1 |
|---|---|---|
|  | (3aR,4S,5S,7S,7aS)-2-[((1R,2R)-2-{[4-(1,2-benzisothiazol-3-yl)piperazin-1-yl]methyl}cyclohexyl)-methyl]-5-hydroxy-5-ethylhexahydro-1H-4,7-methanoisoindole-1,3-dione | 537.2867 |
|  | (3aS,4S,5R,7S,7aR)-2-[((1R,2R)-2-{[4-(1,2-benzisothiazol-3-yl)piperazin-1-yl]methyl}cyclohexyl)-methyl]-5-hydroxy-5-ethylhexahydro-1H-4,7-methanoisoindole-1,3-dione | 537.2863 |

TABLE 1-continued

| Compound | Nomenclature | MS M + 1 |
|---|---|---|
| 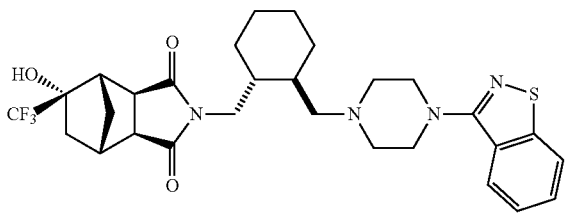 | (3aR,4S,5S,7S,7aS)-2-[((1R,2R)-2-{[4-(1,2-benzisothiazol-3-yl)piperazin-1-yl]methyl}cyclohexyl)-methyl]-5-hydroxy-5-trifluoromethylhexahydro-1H-4,7-methanoisoindole-1,3-dione | 577.2432 |
| 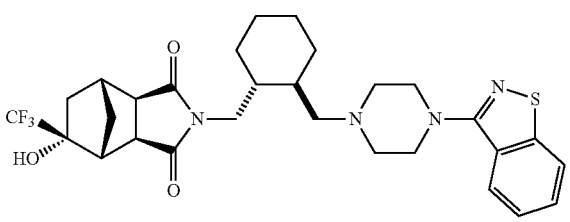 | (3aS,4S,5R,7S,7aR)-2-[((1R,2R)-2-{[4-(1,2-benzisothiazol-3-yl)piperazin-1-yl]methyl}cyclohexyl)-methyl]-5-hydroxy-5-trifluoromethylhexahydro-1H-4,7-methanoisoindole-1,3-dione | 577.2433 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound which is:

or a pharmaceutically acceptable salt thereof.

2. A compound which is:

or a pharmaceutically acceptable salt thereof.

3. A pharmaceutical composition which comprises a pharmaceutically acceptable carrier and the compound of claim 1 or a pharmaceutically acceptable salt thereof.

4. A pharmaceutical composition which comprises a pharmaceutically acceptable carrier and the compound of claim 2 or a pharmaceutically acceptable salt thereof.

5. A method for treating schizophrenia in a human patient in need thereof which comprises administering to the patient a therapeutically effective amount of a compound of claim 1 or a pharmaceutically acceptable salt thereof.

6. A method for treating schizophrenia in a human patient in need thereof which comprises administering to the patient a therapeutically effective amount of a compound of claim 2 or a pharmaceutically acceptable salt thereof.

7. A method for treating bipolar disorder in a human patient in need thereof which comprises administering to the patient a therapeutically effective amount of a compound of claim 1 or a pharmaceutically acceptable salt thereof.

8. A method for treating bipolar disorder in a human patient in need thereof which comprises administering to the patient a therapeutically effective amount of a compound of claim 2 or a pharmaceutically acceptable salt thereof.

* * * * *